US007141550B2

(12) United States Patent
Mölling et al.

(10) Patent No.: US 7,141,550 B2
(45) Date of Patent: Nov. 28, 2006

(54) INTRA-TUMORAL ADMINISTRATION OF IL-12 ENCODING NUCLEIC ACID MOLECULES

(75) Inventors: Karin Mölling, Zürich (CH); Jan Schultz, Zürich (CH); Lucie Heinzerling, Zürich (CH)

(73) Assignee: Universität Zürich Institut für Medizinische Virologie, Zürich (CH)

( * ) Notice: Subject to any disclaimer, the term of this patent is extended or adjusted under 35 U.S.C. 154(b) by 465 days.

(21) Appl. No.: 10/181,794

(22) PCT Filed: Dec. 1, 2001

(86) PCT No.: PCT/EP01/00363

§ 371 (c)(1),
(2), (4) Date: Nov. 26, 2002

(87) PCT Pub. No.: WO01/52874

PCT Pub. Date: Jul. 26, 2001

(65) Prior Publication Data

US 2003/0118564 A1   Jun. 26, 2003

(30) Foreign Application Priority Data

Jan. 20, 2000   (EP) ................................. 00101108

(51) Int. Cl.
*A61K 48/00* (2006.01)
(52) U.S. Cl. ..................... 514/44; 435/320.1; 435/455; 536/23.5
(58) Field of Classification Search ...................... None
See application file for complete search history.

(56) References Cited

FOREIGN PATENT DOCUMENTS

WO   WO 01/52874 A3   7/2001

OTHER PUBLICATIONS

Addison et al, Gene Ther 1998;5:1400-9.*
Tuting et al, Cancer Gene Ther. Jan.-Feb. 1999;6:73-80.*
Lipford et al, Eur J Immunol. Sep. 1997;27:2340-4.*
Gilbert et al, STEP Perspect 1998 Winter;98:15-7.*
Mendiratta, SK. et al., "Intratumoral delivery of IL-12 gene by polyvinyl polymeric vector system to murine renal and colon carcinoma results in potent antitumor immunity" *Gene Therapy*, vol. 6, No. 5:833-839 (1999).
Asselin-Paturel, C. et al., "Transfer of the murine interleukin-12 gene in vivo by a Semliki Forest virus vector induces B16 tumor regression through inhibition of tumor blood vessel formation monitored by Doppler ultrasonography" *Gene Therapy*, vol. 6, No. 4:606-615 (1999).
Budryk, M. et al., "Direct transfer of IL-12 gene into growing Renca tumors" *ACTA Biochimica Polonica*, 47:385-391 (2000) (Abstract).
Moriyama, M. et al., "Mechanical properties of $SiN_xC_y$ ceramic films prepared by plasma CVD" *Journal of Materials Science*, 5:1287-1294 (1991).
Yang, J-P. et al., "Direct gene transfer to mouse melanoma by intratumor injection of free DNA" *Gene Therapy*, vol. 3, No. 3:542-548 (1996) (Abstract).
Witold, L. et al., "Antitumor effects of the combination immunotherapy with interleukin-12 and tumor necrosis factor alpha in mice" *Cancer Immunology Immunotherapy*, vol. 45, No. 2:100-108 (1997) (Abstract).
Nestle, F. O. et al., "Vaccination of melanoma patients with peptide- or tumor lysate-pulsed dendritic cells" *Nature Medicine*, 4:328-332 (1998) (Abstract).
Chu, R. S. et al., "CpG oligodeoxynucleotides act as adjuvants that switch on T Helper 1 (Th1) Immunity", *Journal of Experimental Medicine* vol. 186, No. 10:1623-1631 (1997).
Yasunori, E. et al., "Interleukin-12 (IL-12) enhances antitumor activity of chemotherapy and radiotherapy in murine models." *Proceedings of the American Association for Cancer Research Annual*. vol. 36:480 (1995) (Abstract).
Mullins. D W et al. "Interleukin-12 overcomes paclitaxel-mediated suppression of T-cell proliferation" *Immunopharmacology and Immunotoxicology*, vol. 20, No. 4:473-492 (1998) (Abstract).
Mendiratta, S. K. et al, "Combination of interleukin 12 and interferon alpha gene therapy induces a synergistic antitumor response against colon and renal cell carcinoma" *Human Gene Therapy*, vol. 11, No. 13:1851-1862 (2000) (Abstract).
Schultz, J. et al., "Induction of long-lasting cytokine effect by injection of IL-12 encoding plasmid DNA" *Human Genetics*, 1557-1565 (2000) (Abstract).
Schultz J. et al., "Long-lasting anti-metastatic efficiency of interleukin 12-encoding plasmid DNA" *Human Gene Therapy*, vol. 10, No. 3:407-417 (1999) (Abstract).
Mumper, R. J., "Protective interactive noncondensing (PINC) polymers for enhanced plasmid distribution and expression in rat skeletal muscle" *Journal of Controlled Release*, 52:191-203 (1998).
Luo, D. et al., "Synthetic DNA delivery systems" *Nature Biotechnology*, 18:33-37 (1999).

(Continued)

*Primary Examiner*—Q. Janice Li
(74) *Attorney, Agent, or Firm*—Fish & Neave IP Group of Ropes & Gray LLP; James F. Haley; Jane T. Gunnison (57) ABSTRACT

Described is the use of a nucleic acid molecule encoding an IL-12 polypeptide for the preparation of a pharmaceutical composition for the treatment of a tumor, wherein the pharmaceutical composition is for intra-tumoral administration.

11 Claims, 8 Drawing Sheets

OTHER PUBLICATIONS

Kircheis, R. et al., "Polycation-based DNA complexes for tumor-targeted gene delivery in vivo" *The Journal of Gene Medicine*, 1:111-120 (1999).

Mumper, R. J. et al., "Polyvinyl derivatives as novel interactive polymers for controlled gene delivery to muscle" *Pharmaceutical Research*, vol. 13, No. 5:701-709 (1996).

Confirmation of receipt of publication date for vol. 47, No. 2/2000 of *Acta Biochimica Polnica*.

Results of Clinical Trials using intra-tumoral administration of naked DNA encoding IL-12, as submitted by Dr. Karin Mölling in PCT/EPO1/00363 on Feb. 2, 2002.

Gao, P. et al., "TGF beta 1 on murine tumor growth following direct intratumoral injection of plasmid DNA" *Zhonghua Zhong Liu Za Zhi*, vol. 19, No. 2:93-5 (1997).

Goto, T. et al., "Highly effective electro-gene therapy of solid tumor by using an expression plasmid for the herpes simplex virus thymidine kinase gene", *Procedings of National Academy of Science U.S.A.*, vol. 97, No. 1:354-9. (2000).

Hauses, M. et al., "Gene therapy and gastrointestinal cancer: concepts and clinical facts", vol. 384, No. 5:479-88. (1999) (Abstract).

Hauses, M. et al., "Gene therapy and gastrointestinal cancer: concepts and clinical facts", vol. 384, No. 5:479-88. (1999).

Kouraklis, G. et al., "Progress in cancer gene therapy", Acta Oncology, vol. 38, No. 6:675-83 (1999).

Sussman et al., "The structural basis for molecular recognition by the vitamin $B_{12}$ RNA aptamer" *Nature Structural Biology*, 7: 53-57 (2000).

Okazawa et al., "In vitro selection of hematoporphyrin binding DNA aptamers" *Bioorganic & Medicinal Chemistry Letters*, 10: 2653-56 (2000).

Romig et al., "Aptamer affinity chromatography: combinatorial chemistry applied to protein purification" *Journal of Chromatography B*, 731: 275-284 (1999).

Sun, "Technology evaluation: SELEX, Gilead Sciences Inc" *Current Opinion in Molecular Therapeutics*, 2: 100-105 (2000).

\* cited by examiner

INTRA-TUMORAL ADMINISTRATION OF IL-12 ENCODING NUCLEIC ACID MOLECULES

The present invention relates to the use of a nucleic acid molecule encoding an IL-12 polypeptide, in particular a p75 heterodimer comprising two subunits, i.e. p40 and p35, for the preparation of a pharmaceutical composition for the treatment of a tumor, wherein the pharmaceutical composition is for intra-tumoral administration.

Cancer is still one of the main causes of death in mankind. Therefore, a lot of research is done in order to understand the origin of cancer and to develop methods for prevention and/or treatment of the various kinds of cancer.

One type of molecules which has been tested as anticancer agents are cytokines such as IL-2, GM-CSF and IL-12. In this regard IL-12 showed superior anti-tumor activity (Rakhmilevich et al., Hum. Gene Ther. 8 (1997), 1303–1311). In previous immunotherapy of tumors recombinant IL-12 protein has been used. However, short-lasting efficiency with high concentrations created considerable side effects. In a human Phase I study intravenous application of (rh) IL-12 lead to hematological toxicity, hyperglycemia, hypoalbuminemia, alteration of liver function and even death as well as fever/chills, fatigue, nausea, vomiting and headaches (Atkins et al., Clin. Cancer Research 3 (1997), 409–417). In order to avoid these side effects approaches were tested using intradermal or intramuscular administration IL-12 encoding DNA. For example, intramuscular injection of DNA encoding IL-12 prevented metastasis formation of mouse malignant melanoma (Schultz et al., Hum. Gene Ther. 10 (1999), 407–417). Although these approaches showed promising effects, they were not efficient enough to allow a successful treatment of tumors with a long-lasting effect and without negative side effects.

Thus, the technical problem underlying the present invention is to provide means for a more efficient treatment of tumors.

This problem is solved by the provision of the embodiments as defined in the claims.

Therefore, the present invention relates to the use of a nucleic acid molecule encoding an IL-12 polypeptide for the preparation of a pharmaceutical composition for the treatment of a tumor, wherein the pharmaceutical composition is for intra-tumoral administration.

It has been surprisingly found that the intra-tumoral application of IL-12 encoding DNA leads to a significant growth retardation and to a drastic and long-lasting tumor regression. More surprisingly, the intra-tumoral application of IL-12 DNA does not lead to the severe side effects observed with the direct application of the IL-12 polypeptide.

The term "nucleic acid molecule" refers to any possible nucleic acid molecule encoding an IL-12 polypeptide, e.g. RNA or DNA, linear or circular, single stranded or double stranded, modified or unmodified. In a preferred embodiment the nucleic acid is DNA. Preferably, the DNA is a double stranded DNA, more preferably a circular one, and even more preferably a plasmid.

In a further preferred embodiment the nucleic acid molecule is linked to (a) peptide(s) which facilitate(s) transfer of a nucleic acid molecule into eukaryotic cells. Such a peptide is preferably a peptide as described in WO 94/23751. Alternatively, such a peptide may comprise a nuclear localization sequence (NLS). Such sequences are described in the literature, for example, in Efthymiadis et al. (J. Biol. Chem. 272 (1997), 22143–22139), Dang and Lee (J. Biol. Chem. 264 (1989), 18019–18023), Liang and Clarke (J. Biol. Chem. 274 (1999), 32699–32703), Tagawa et al. (J. Cell Biol. 30 (1995), 255–263), Truant and Collen (Mol. Cell. Biol. 19 (1999), 1210–1217), Moreland et al. (Mol. Cell. Biol. 7 (1987), 4048–4057). The peptide may be linked to the nucleic acid molecule, e.g., covalently or by ionic interaction, hydrophobic interaction, van der Waals bonding etc. The linkage between the nucleic acid and the peptide is preferably as described in WO 94/23751.

In a particularly preferred embodiment the DNA is unpackaged DNA. In this context the term "unpackaged DNA" means DNA in an aqueous solution without viral vectors. The DNA solution may contain stabilizers or agents for protection against nucleases.

In a further particularly preferred embodiment the DNA is naked DNA. "Naked" in this regard means that the DNA is not complexed to viral structures, proteins or liposomes or the like, most preferably the DNA is present in fluid medium which does not contain any components apart from water and a buffer.

The term "IL-12 polypeptide" means any polypeptide having IL-12 activity. IL-12 has been extensively described in the literature and, e.g., in EP-B1 433 827 and EP-A1 790 308. It is a heterodimer of about 75 kD comprised of two polypeptide subunits, a 40 kD subunit and a 35 kD subunit, which are bonded together via one or more disulfide bonds. A polypeptide having IL-12 activity is in particular a polypeptide having at least one of the following characteristics:

(a) as a biological mediator, IL-12 can activate NK-cells;
(b) it can enhance cellular immune mechanisms by directing $CD4^+$ T-cells towards a TH1-type response;
(c) it can stimulate interferon-γ and interleukin-2 secretion;
(d) it can increase immunogenicity of the tumors by upregulating HLA class I, HLA class II and ICAM-I expression on human melanoma cells; and
(e) it has antiangiogenic properties.

To evaluate a potential antitumor effect of intramuscular IL-12 DNA therapy a fibrosarcoma animal model can be applied using MC57 cells in C57BL/6 mice.

The IL-12 polypeptide may be of any organism producing such a polypeptide, preferably of mammals, e.g. mice, most preferably of humans.

Nucleic acid molecules encoding IL-12 are known. EP-B1 433 827, e.g., discloses the cDNA sequence encoding human IL-12. Schultz et al. (Hum. Gen. Ther. 10 (1999), 407–417) discloses a plasmid containing the murine IL-12 cDNA.

Preferably, the nucleic acid molecule codes for both subunits of the IL-12 heterodimer.

In a preferred embodiment the IL-12 polypeptide is the heterodimer comprising both subunits, more preferably it is a human IL-12 polypeptide, more preferably the IL-12 polypeptide having the amino acid sequence as disclosed in Genebank Accession Nos. AF 180563 (p40) and NM 000882 (p35) or in Gubler et al. (Proc. Natl. Acad. Sci. USA 88 (1991), 4143–4147). In a particularly preferred embodiment the nucleic acid molecule encoding an IL-12 polypeptide is the cDNA encoding human IL-12.

In the context of the present invention the term "tumor" means any possible tumor. In a preferred embodiment the tumor is a highly vascularized tumor. The term "highly vascularized" means that the tumor contains blood vessels and can form new blood vessels for more blood supply (angiogenesis) and tumor growth.

Examples for such tumors are carcinomas (colon, breast, lung, pancreatic, squamous cell, head and neck, adeno, renal cell, etc.) and sarcomas (fibro-, bone, Ewing, Kaposi, etc.) and mastocytoma, basalioma, haemangioma, etc.

In a particularly preferred embodiment the tumor is a melanoma tumor. Melanoma represents a tumor entity with rising incidence (Dennis et al., Arch. Dermatol. 135 (1999), 275–280). Prognosis of disease in general depends on the thickness of the primary tumor at the time of diagnosis. When diagnosed in early stages excision with a security margin can be curative. However, once metastasized to date no therapy has been shown to lead to tumor eradication.

Currently, two major immune therapeutic approaches are evaluated for their effectiveness against advanced melanoma: (i) Vaccination with tumor associated antigens and peptides thereof to induce or enhance the activity of tumor specific cytotoxic lymphocytes (Marchand et al., Int. J. Cancer 80 (1999), 219–230; Nestle et al., Nat. Med. 4 (1998), 328–332; Jaeger et al., Int. J. Cancer 66 (1996), 162–169), (ii) Stimulation of the immune response to the tumor with co-stimulatory molecules and cytokines such as IL-2, IFN-a, GM-CSF and IL-12 (Dummer et al., Cancer 75 (1995), 1038–1044; Agarwala et al., Ann. Surg. Oncol. 2 (1995), 365–371; Leong et al., J. Immuntherap. 22 (1999), 166–174; Lotze et al.; Ann. NY Acad. Sci. 795 (1996), 440 –454). In malignant melanoma a number of tumor associated antigens have been identified (MAGE, MART, gp100, Tyrosinase; Rosenberg et al., Immunol. Today 18 (1997), 175–182).

Vaccination with tumor associated antigens is however dependent on and thus restricted by the HLA type of the patient (Nestle et al. (1998), loc. cit.). Furthermore, immune escape mechanisms by selection of tumor cells with low immunogenicity often impeded long-lasting results (Geertsen et al., Int. J. Mol. Med. 3 (1999), 49–57). Cytokines such as IL-2 and IFN-α have been widely used to treat malignant melanoma. Their effects can act synergistically in vitro and possibly in vivo in cancer immune therapy including melanoma (Keilholz et al., Cancer 72 (1993), 607–614). In current clinical studies these proteins are being used in combination with chemotherapy. However, a major drawback of systemic therapies with recombinant cytokines are their short half life time and their toxicity (Bear at el., Semin. Surg. Oncol. 12 (1996), 436–445).

It was now surprisingly found that the intra-tumoral injection of DNA encoding IL-12 leads to a drastic regression of tumor growth and had a long-lasting effect. Furthermore, no negative side effects were observed.

In the context of the present invention the term "intratumoral administration" means that the nucleic acid molecule encoding IL-12 is delivered directly into the tumor, i.e. into actively dividing tumor cells surrounding the necrotic central part of the tumor and not, e.g., only into peritumoral cells or into the center of the tumor. The term "tumor" in this context does not only refer to the primary tumor but also to metastases. Appropriate means for intratumoral administration are, e.g., injection, ballistic tools, electroporation, electroinsertion, wounding, scratching, pressurized insertion tools, dermojets, etc.

In a preferred embodiment, intra-tumoral administration is carried out by injection, preferably by a needle and a syringe. In this case the nucleic acid molecule encoding IL-12 is contained in a solution which can be administered by a syringe. A suitable solution in this regard is, e.g., phosphate buffered saline (PBS), citrate buffer, Tris-HCl buffer or any physiological buffer.

Preferably, the nucleic acid molecule encoding IL-12 is administered more than once. In particular, it can be advantageous to administer the nucleic acid molecule by intratumoral administration repeatedly, e.g. at least twice or three times, on day 1, 3 and/or 5. When administration is carried out by injection, more than one injection is preferred (e.g. five to six injections). Furthermore, the needle is preferably inserted tangential to the tumor and is not pointing to the center of the tumor. An example for a therapy protocol is 50 μg of DNA as a predose, 7 days before a triple dose, i.e. 3 doses at day 1, 3, 5 or 1, 8, 15. The triple dose can be repeated after 2 or 3 weeks, it can also be repeated several times (3 or 4 times) and repeated when the tumor comes back. Thus, the treatment may consist of one, two or more cycles.

The amount of the nucleic acid molecule to be administered depends, e.g. on the length of the nucleic acid molecule, on the body weight of the organism to be treated and on the size of the tumor. Generally, about 5 to 500 μg plasmid-DNA containing and IL-12 encoding cDNA are used, preferably 20 to 300 μg, more preferably 50 to 250 μg.

It is particularly preferred that a predose of the nucleic acid molecule encoding IL-12 is administered about 14 days before the actual treatment starts. Preferably, the predose comprises about 50 μg of naked plasmid DNA. Such a predose prevents toxic side effects of the administered compound (Leonard et al., Blood 90 (1997), 2541–2548).

A particularly preferred embodiment for the mode of administration is a regimen in which the administration of the predose is followed by two cycles of administration and wherein in cycle one 100 μg to 750 μg of naked plasmid DNA are administered on days 1, 8 and 15 and wherein in cycle two 200 μg to 1000 μg of naked plasmid DNA are administered on days 23, 36 and 43.

In another preferred embodiment of the present invention the intra-tumoral administration of a nucleic acid molecule encoding IL-12 is combined with the administration of another cytokine. In this way the anti-tumor effect of IL-12 can be enhanced. The administration of the other cytokine can be achieved, e.g., by administering a nucleic acid molecule encoding the respective cytokine or by administering the respective cytokine itself.

In a preferred embodiment the other cytokine is selected from the group consisting of IL-15, IL-2, IP-10, GM-CSF, IFN-α (interferone α), TNF (tumor necrosis factor) and PAI-1 (plasminogen activator inhibitor 1).

In a further preferred embodiment the intra-tumoral administration of a nucleic acid molecule encoding IL-12 is combined with the administration of a tumor-associated antigen (TAA). The administration of the TAA may be achieved, e.g., by administering a nucleic acid molecule encoding the respective TAA or by administering the respective TAA itself. The TAA is preferably a TAA which is associated with the tumor to be treated. Examples of TAAs and corresponding types of tumors are shown in the following list:

| | |
|---|---|
| melanoma: | gp100, tyrosinase, MAGE-1, MAGE-3, MART, BAGE, TRP-1 |
| stomach cancer: | CEA (carcino embryonic antigen), CA 19-9, CA 50, CA 72-4 |
| Colon cancer: | CEA, CA 19-9, Muc-1 |
| pancreas carcinoma: | CA 19-9, Ca-50, CEA |
| small cell | CEA, NSE (neuron specific enolase), |

-continued

| | |
|---|---|
| lung cancer: | EGF-receptor |
| lung cancer: | CEA |
| liver carcinoma: | α-fetoprotein (AFP) |
| prostata cancer: | PSA |
| gall bladder cancer: | CA 19-9 |
| Squamous cell carcinoma: | SSC (squamous cell carcinoma antigen), CEA |
| Mammary carcinoma: | CA 15-3, CEA, BRCA-1, BRCA-2, Muc-1, Her2/Neu receptor |
| Testes cancer: | AFP, hCG |
| ovarial carcinoma: | CA-125, CEA, CA 15-3, AFP, TAG-72 |
| B cell lymphoma: | CD20, CD21 |

In a further preferred embodiment the nucleic acid molecule encoding IL-12 is administered together with C- and G-rich single- or double-stranded oligonucleotides, such as CpG oligonucleotides. Such oligonucleotides are preferably about 20 nucleotides long with CpG in the center surrounded by sequences which may be palindromic (see e.g. Schultz et al., Human Gene Therapy 10 (1999), 407–417; Chu et al., J. Exp. Med. 186 (1997), 1623–1631). Other double- or single-stranded DNA oligonucleotides, e.g., are aptamers, about 14 nucleotides long which bind to, e.g., integrins and show an antiproliferative effect (Bachmann et al., Molecular Med. 76 (1998), 126–132), or DNA oligonucleotides as described in WO 94/23751.

In yet another preferred embodiment the nucleic acid molecule encoding IL-12 is administered together with peptides, in particular with peptides from tumor-associated antigens.

Finally, the pharmaceutical composition prepared according to the use of the invention can be applied in combination with a chemotherapy treatment, such as an anti-cancer chemotherapy or an HAART (highly active anti-retroviral HIV therapy).

The present invention also relates to the use of a nucleic acid molecule encoding an IL-12 polypeptide for the treatment of a tumor by intra-tumoral administration as well as to a method for the treatment of a tumor by intra-tumoral administration of a nucleic acid molecule encoding an IL-12 polypeptide. With respect to the preferred embodiments, the same applies as set forth above for the use according to the invention.

The treatment may comprise one, two or more cycles of administration.

In a preferred embodiment the treatment comprises the administration of a predose about 14 days before the actual treatment starts. Preferably, the predose comprises about 50 µg of naked plasmid DNA comprising a nucleic acid sequence encoding IL-12.

In a further preferred embodiment the administration of a predose is followed by a regimen which comprises two cycles and wherein in cycle one 100 µg to 750 µg of naked plasmid DNA are administered on days 1, 8 and 15 and wherein in cycle two 200 µg to 1000 µg of naked plasmid DNA are administered on days 29, 36 and 43.

All references cited herein are herewith incorporated by reference.

FIG. 1 shows tumor growth after intramuscular injection of DNA. Mean tumor volumes and standard deviation of subcutaneous B16-F10-melanoma in C57Bl/6 mice during and in the follow-up of plasmid DNA injection. $2 \times 10^5$ exponentially growing B16F10-melanoma cells were injected subcutaneously in flanks of C57Bl/6 mice and formed tumors after 9 days. Animals were injected at mean tumor diameter of 5 mm intramuscularly on day 1, 3 and 5 with VR1012-muIL12 (n=7; black squares) or empty vector (n=6; open rhombus).

FIG. 2 shows tumor growth retardation by intratumoral injection of DNA. Mean tumor volumes and standard deviation of subcutaneous B16-F10-melanoma in C57BL/6 mice. $2 \times 10^5$ exponentially growing B16F10-melanoma cells were injected subcutaneously in flanks of C57Bl/6 mice and formed tumors after 9 days. Animals were injected at mean tumor diameter of 5 mm intratumorally on day 1, 3 and 5 with VR1012-muIL12 (n=7; open squares) or empty vector (n=6; open rhombus). * implies significant difference (p<0.05) when compared with other group with Student's t-test.

FIG. 3 shows tumor regression of human melanoma by intratumoral injection of cytokine encoding DNA. Mean tumor volumes and standard deviation of subcutaneous human MeMM 941209-melanoma in Balb/c nu/nu mice. $2 \times 10^5$ exponentially growing human MeMM 941209-melanoma cells were injected subcutaneously in flanks of nude mice and formed tumors after 18 days. Animals were injected at mean tumor volume of 500 mm$^3$ intratumorally on day 1, 3 and 5 with VR1012 muIL12 (n=5; open square) or empty vector (n=5; open rhombus). * implies significant difference (p<0.05) when compared with other group with Student's t-test.

FIG. 4 shows histologic changes in angiogenesis after intratumoral vaccination with DNA coding for murine IL-12 into human melanoma (see FIG. 3). (A) Hematoxillin-eosinophil staining of biopsy taken from control mouse (B) Hematoxillin-eosinophil staining of biopsy taken from mouse injected with DNA coding for IL-12 (C) PAS staining of biopsy taken from control mouse (D) PAS staining of biopsy taken from mouse injected with DNA coding for IL-12. (Magnification and bar corresponding size: A 200×, 20 µm; B 400×, 10 µm; C 25×; D 100×, 40 µm).

FIG. 5 shows that the tumor therapeutic effect is not completely abrogated by depleting NK-cells. Mean tumor volumes and standard deviation of subcutaneous human MeMM 941209-melanoma in Balb/c nu/nu mice depleted of natural killer (NK–) cells. $2 \times 10^5$ exponentially growing human MeMM 941209-melanoma cells were injected subcutaneously in flanks of nude mice and formed tumors after 10 days. NK-cell depletion was realized by injecting anti-asialo GM1 antibodies intraperitoneally 3 days and 24 hours before starting treatment. Animals were injected at a mean tumor diameter of 4 mm intratumorally on day 1, 3 and 5 with VR1012-muIL12 (n=5; squares) or empty vector (n=5; open rhombus). * implies significant difference (p<0.05) when compared with other group with Student's t-test.

FIG. 6 shows the effect of plasmid DNA treatment on the development of white horse melanoma metastasis. White horses that had developed metastatic melanoma spontaneously were injected intratumorally on day 1, 3 and 5 of each treatment cycle with 250 µg of plasmid DNA coding for human IL-12 (A, B) or 250 µg of plasmid DNA with the reverse human IL-12 insert (C). Some marker lesions were left untreated to determine tumor evolvement without treatment (D). Punch or trucat biopsies were performed on all marker and treated metastasis and biopsy specimens were examined histologically before therapy and on day 14 and 30. Tumors were measured using calipers and by ultrasound (US) and tumor volumes were calculated according to the formula: small diameter$^2$×large dimater×0.5.

The following examples serve to further illustrate the invention.

EXAMPLE 1

Intra-tumoral Injection of IL-12 Encoding Plasmid DNA into Human and Murine Melanoma Tumors Plasmid DNA. The murine IL-12 cDNAs was a gift from M. Gately (New Jersey, USA) and subcloned by S. Hemmi (Zurich) from pBLKs IRES-muIL-12, into the BamHI restriction site of the backbone. The plasmid VR1012-muIL-12 contains the cDNA of murine IL-12 under the control of the CMV immediate early enhancer/promoter region (Schultz et al., Hum. Gene Ther. 10 (1999), 407–417). The two subunits of IL-12, p 35 and p 40, are linked by an internal ribosomal entry site (IRES). Plasmid DNA was purified with Qiagen columns (QIAGEN GmbH, Hilden, Germany) using endotoxin free reagents according to the supplier's protocol. It was dissolved in PBS and injected at 50 μg/50 μl. Expression of both subunits in serum samples after intramuscular plasmid DNA injection has been verified using commercially available ELISA kits (Genzyme, Biosource). Expression of IL-12 protein after intratumoral plasmid DNA injection has been measured in the serum using commercially available ELISA kits (Genzyme, Biosource). The detection limits of the ELISA assays used were 5 pg/ml, Genzyme, and 15 pg/ml, Biosource, respectively. Mice and tumors. C57BL/6 mice and BALB/c nu/nu were bred in our animal facilities. The metastatic murine melanoma cell line B16F10, a gift from M. Burger, Basel, were grown in Dulbecco's Modified Eagles Media (DMEM), supplemented with 10% fetal calf serum (FCS), 100 μg/ml streptomycin, 100 IU/ml penicillin and 1 mmol/ml L-glutamine. The human melanoma cell culture MM 941209 was established as described earlier (Yue et al., Int. J. Cancer 71 (1997), 630–637). MM 941209 cells were grown in RPMI 1640 complete medium supplemented with 10% fetal calf serum (FCS), streptomycin (100 ml/ml), penicillin (100 IU/ml) and L-glutamine (1 mmol/ml). For tumor inoculation into the mice exponentially growing B16-F10 cells or MM 941209 cells were harvested by trypsinization, washed twice with PBS and 1×10$^5$ viable cells as determined by the trypan blue dye exclusion were injected subcutaneously into C57BL/6 and BALB/c nu/nu mice respectively. When subcutaneous tumors had established mice were injected intralesionally on days 1, 3 and 5. Plasmid DNA was dissolved in PBS to amount to a total volume of 50 μl and 50 μg of DNA for each dose. Tumor measurement was performed every other day using calipers. Tumor volume was calculated according to the formula: 0.5×larger diameter×(smaller diameter)$^2$.

Antibodies. Biopsies for histologic evaluation and immunhistochemistry were taken at days 9, 13, 16 and 19 in the C57BL/6 mice and at day 12 or 14 in the Balb/c nu/nu mice. NK-cell depletion was performed by intraperitoneally injecting 30 μl of polyclonal rabbit anti-asialo GM 1 antibodies, WAKO Chemicals (Osaka, Japan), into the mice three days and 24 hours prior to the DNA treatment. Hematoxyllin-Eosin and PAS stainings were performed on paraffin-embedded tissue sections.

CD 4, CD 8 (antibodies purchased at Pharmingen) and CD 31 (antibodies purchased at Beckton and Dickinson) stainings were performed on cryostat sections.

Statistical analyses

Results are presented as mean +/− standard deviation (SD) of the mean. Differences between means were analyzed using the unpaired Student's t-test (two-tailed). None of the animals was excluded from analysis. The probability value $p<0.05$ was considered statistically significant.

Figure 1:
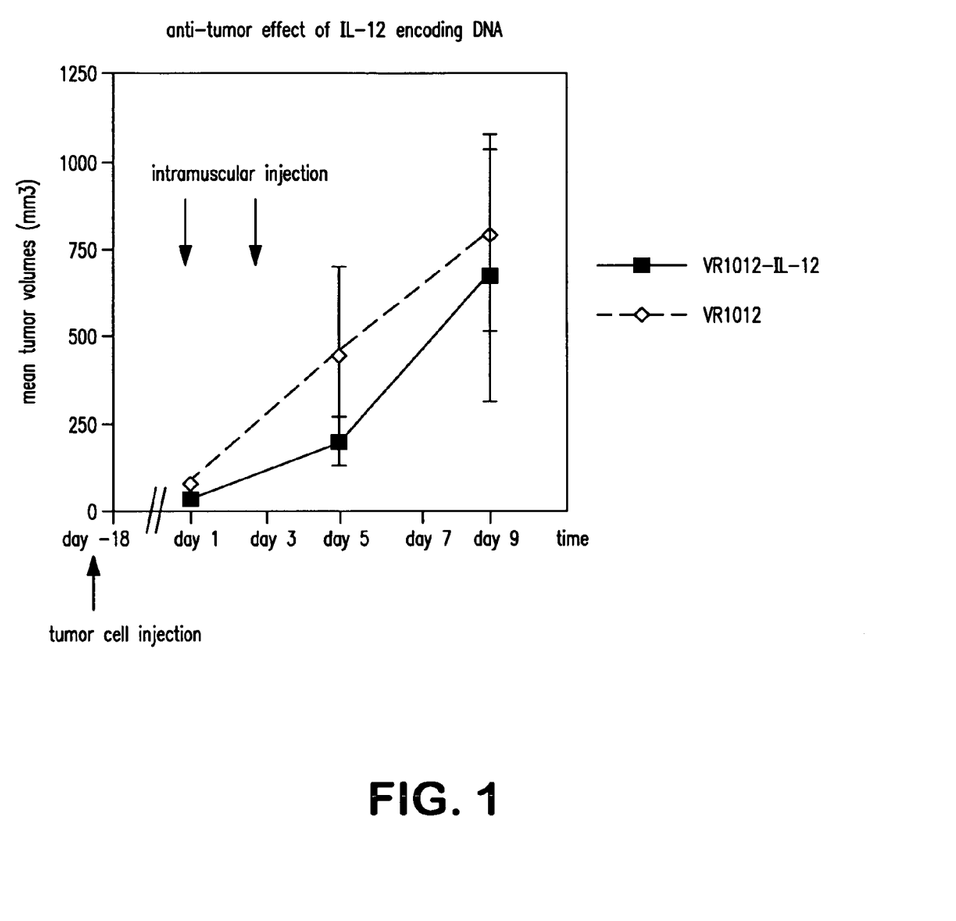

The well-described B16-F10 cell line was injected subcutaneously into C57BL/6 mice. At a mean tumor size of 55 mm$^3$ as measured with calipers DNA treatment was started by intramuscular injection of VR1012 plasmid DNA coding for both subunits of IL-12, p40 and p35. In the eukaryotic expression vector used the cDNA was under the direction of the human cytomegalovirus (CMV)-immediate early (IE-1) promoter/enhancer region as described earlier (Schultz et al., loc. cit.). Intramuscular injection of this vector induced expression of the two subunits and measurable levels of the bioactive IL-12-heterodimer in vivo. Empty plasmid DNA without IL-12 insert used as control did not result in measurable serum IL-12 levels (Schultz et al., loc. cit.). Intramuscular injection was carried out by injecting plasmid DNA into the quadriceps of the mice. Treatment was performed once on day 1 at a mean tumor volume of 55±22 mm$^3$. The results of this experiment are shown in FIG. 1. Differences in tumor growth between the group injected with the control vector and the group injected with the plasmid encoding IL-12 could not be seen up to day 9. Therefore a change in mode of application was undertaken.

Figure 2:
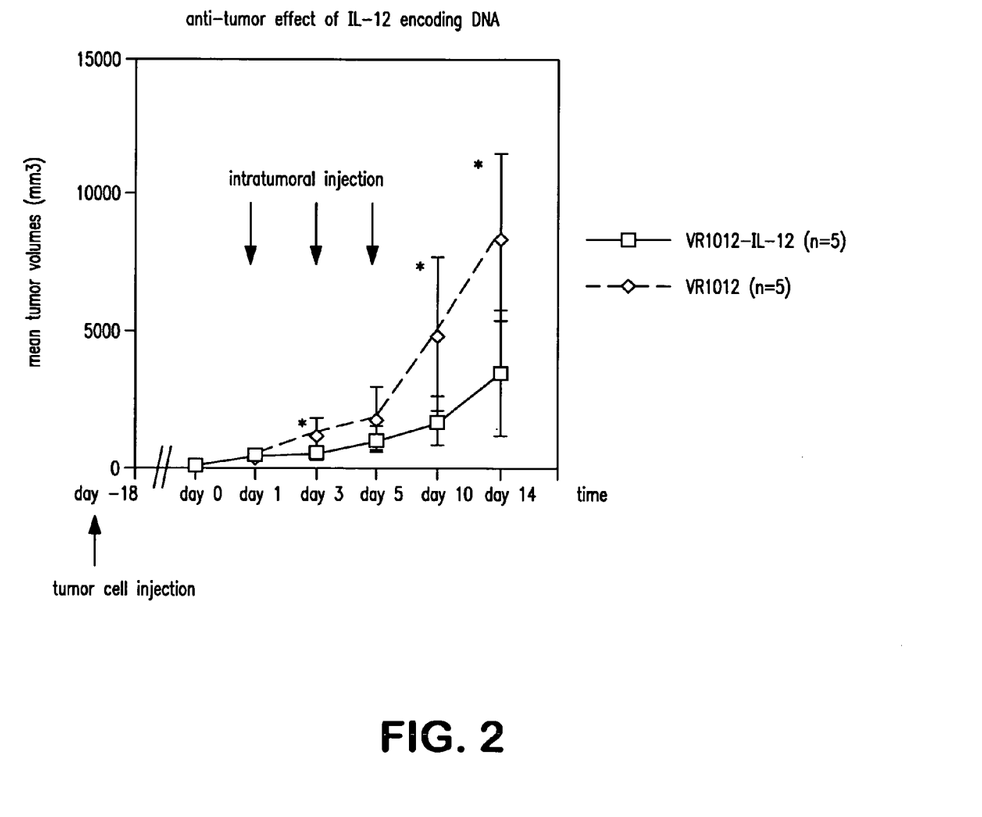

Direct injections into subcutaneous B16-melanoma tumors were started at a mean tumor volume of 158 mm$^3$ in the treatment group and 139 mm$^3$ in the control group. Intratumoral injections at a dose of 50 μg of plasmid DNA each were administered on day 1, 3 and 5. After two days a significant difference in tumor volumes between the two groups was observed resulting in less than a third of the mean tumor volume in the treatment group compared to the control group (FIG. 2). This effect was further accentuated over the time course resulting in a final mean tumor volume of 3482 mm$^3$ in the group treated with DNA coding for IL-12 as opposed to 8428 mm$^3$ in the control group after 14 days.

Primary, secondary and metastatic tumors resected from patients were trypsinized and propagated in vitro. Exponentially growing cells were injected subcutaneously into Balb/c nude mice applicating 1×10$^5$ viable cells. Only one out of 3 tumor cell cultures (MM 941209, MM 950504, MM 960104) resulted in tumors after subcutaneous injection of the cells in the flank of the animals. In the cell line which formed tumors, MM 941209, it was not possible to upregulate HLA class I or induce HLA class II and ICAM by stimulating with murine or human interleukin 12 for 48 hours though it was slightly positive for IL-12 receptor (results not shown).

Figure 3:
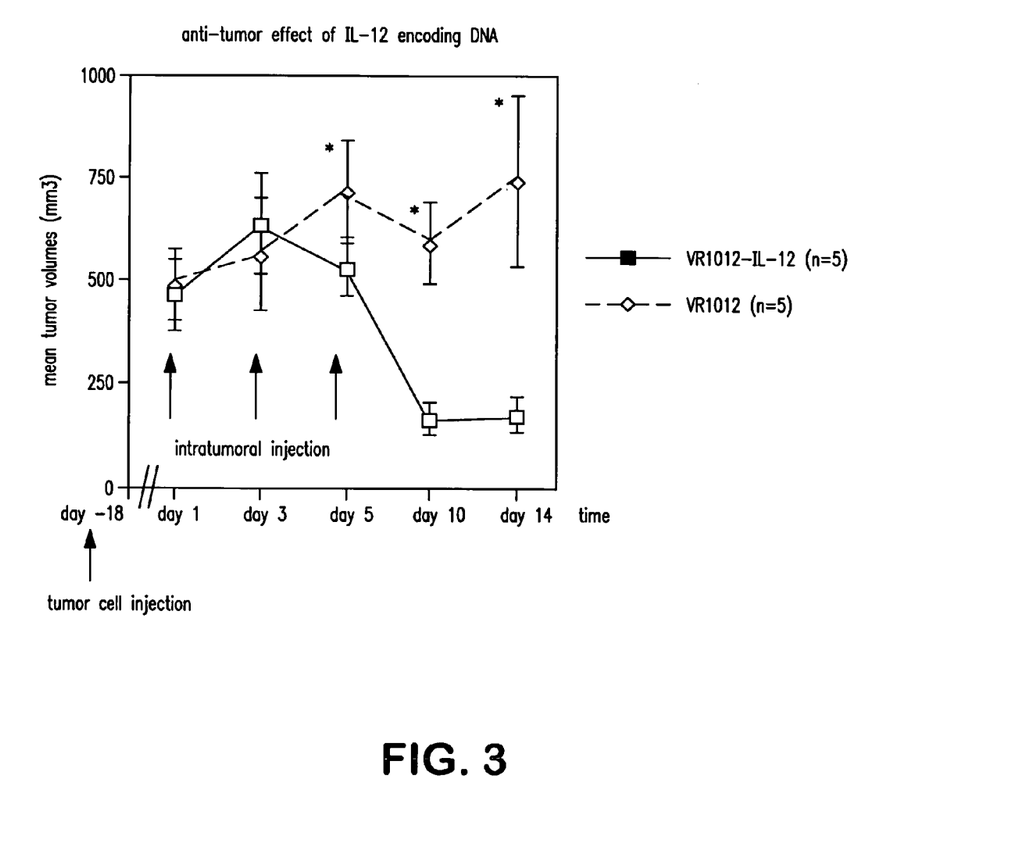
Figure 4A:
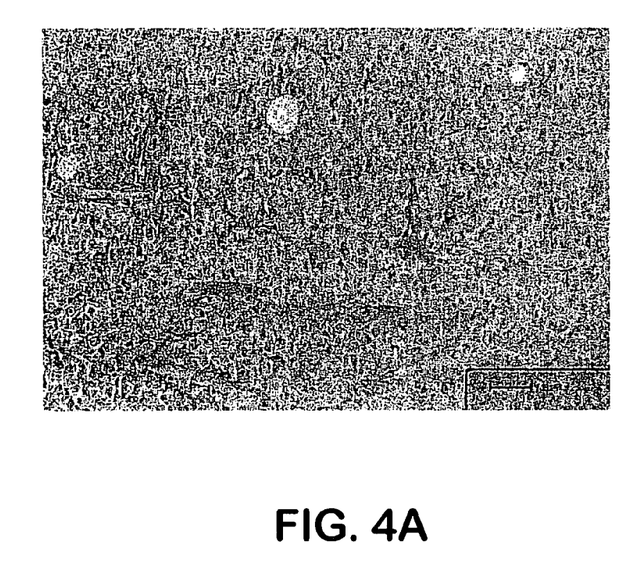
Figure 4B:
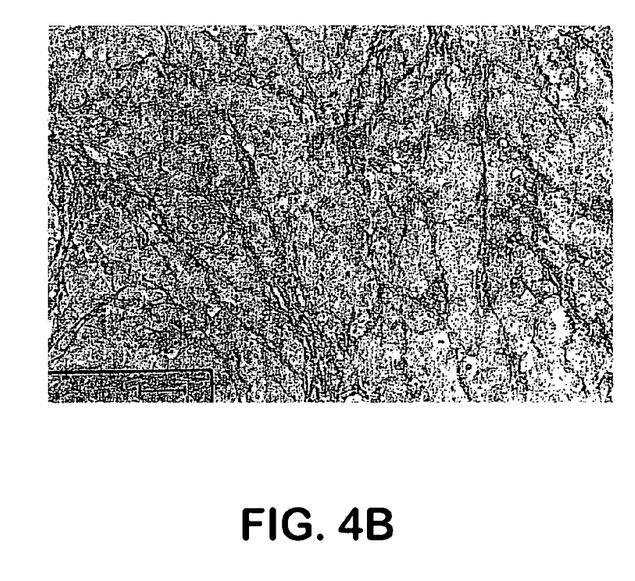
Figure 4C:
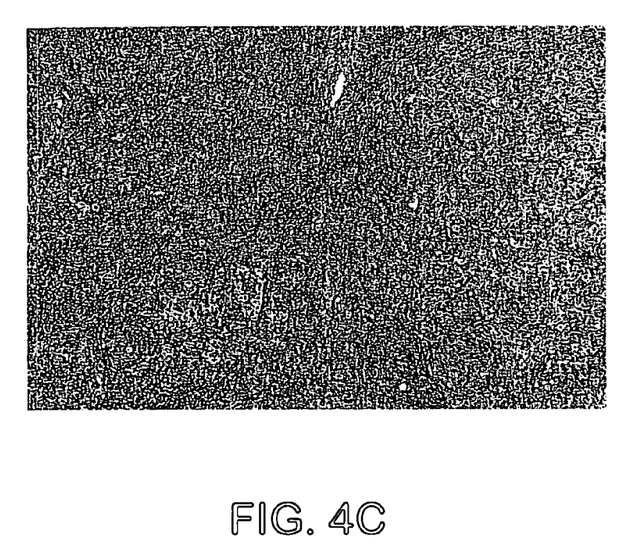
Figure 4D:
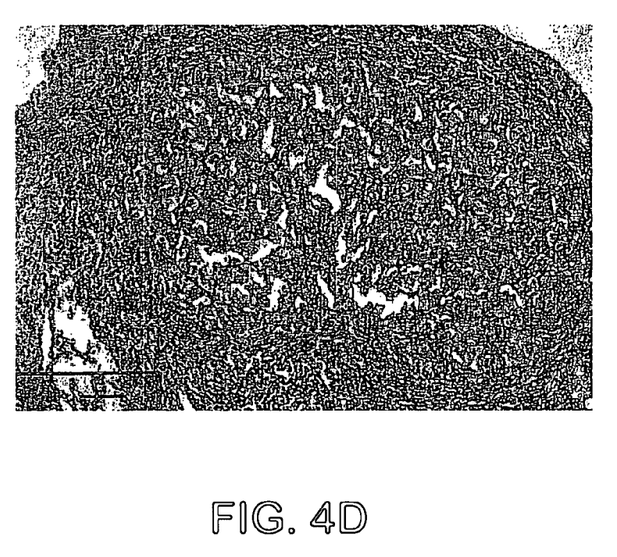

Injections directly into human MM 941209 melanomas of nude mice were started at a mean tumor volume of 461±87 mm$^3$ in the treatment group and 486±88 mm$^3$ in the control group. Intratumoral injections of 50 mg plasmid DNA were administered on day 1, 3 and 5. Until day 3 the group treated with DNA coding for IL-12 showed a slightly bigger increase in tumor volumes. From day 5 on there was a marked decrease in tumor volumes in the treatment group (FIG. 3). On day 14 two out of five treated animals were tumor free as verified by thorough histologic examination. Mean tumor volume of the three other animals was 175±44 mm$^3$. The control group showed a striking increase of tumor volumes up to a mean of 740±208 mm$^3$.

EXAMPLE 2

Determination of Serum Levels of IL-12 Protein

In order to determine serum levels of IL-12 protein blood samples were taken from the tail vein of the C57BL/6 mice described in Example 1 on day 0, 3, 5, 10 and 14. In the serum probes no significant differences in expression of total IL-12 as measured by concentrations of p40 IL12 in ELISA assays was found between mice treated intralesionally with IL-12 encoding DNA and empty plasmid treated mice (results not shown). Thus in contrast to intramuscular application, intratumoral injection of plasmid DNA coding for IL-12 does not induce detectable systemic expression of the protein. Assessment of IL-12 protein levels in the serum of nude mice were not undertaken to avoid the risk of infection.

EXAMPLE 3

Histological and Immunhistochemical Analysis of Tumor Specimens

The biopsies were collected on days 9, 13, 16 and 19 in the C57BL/6 mice and at day 12 or 14 in the Balb/c nude mice described in Example 1 and analyzed by light microscopy.

In the biopsies from B16 melanoma tumors injected intralesionally with DNA encoding IL-12 a rich peritumoral infiltrate consisting mainly of CD4- but also of CD8-positive lymphocytes was observed. Some tumor infiltrating lymphocytes could be seen in the treated tumors.

The tumors collected from the nude mice were morphologically not differentiable from normal human melanoma. They showed positive staining for HMB 45 the antibody specifically binding to gp100/pmel 17, Melan A and tyrosinase (not shown). In the treatment group consisting of the animals with subcutaneous human MM 941209 the pattern of the vasculature in the tumors as analyzed in PAS and anti-CD31 stainings of these animals also differed significantly when compared to the controls injected with control plasmid DNA only (FIG. 4). In the IL-12 DNA treated group endothelial thickening, clotting within the lumen and abrupt changes of diameter of the vessels were present. In the control group a regular pattern with smooth skinny endothelial walls and no clotting in the vessels was seen. The three treated tumors that still existed presented with large areas of necrosis. In two out of five animals no tumor cells could be seen in the biopsy specimen.

EXAMPLE 4

Depletion of NK-cells

Figure 5:
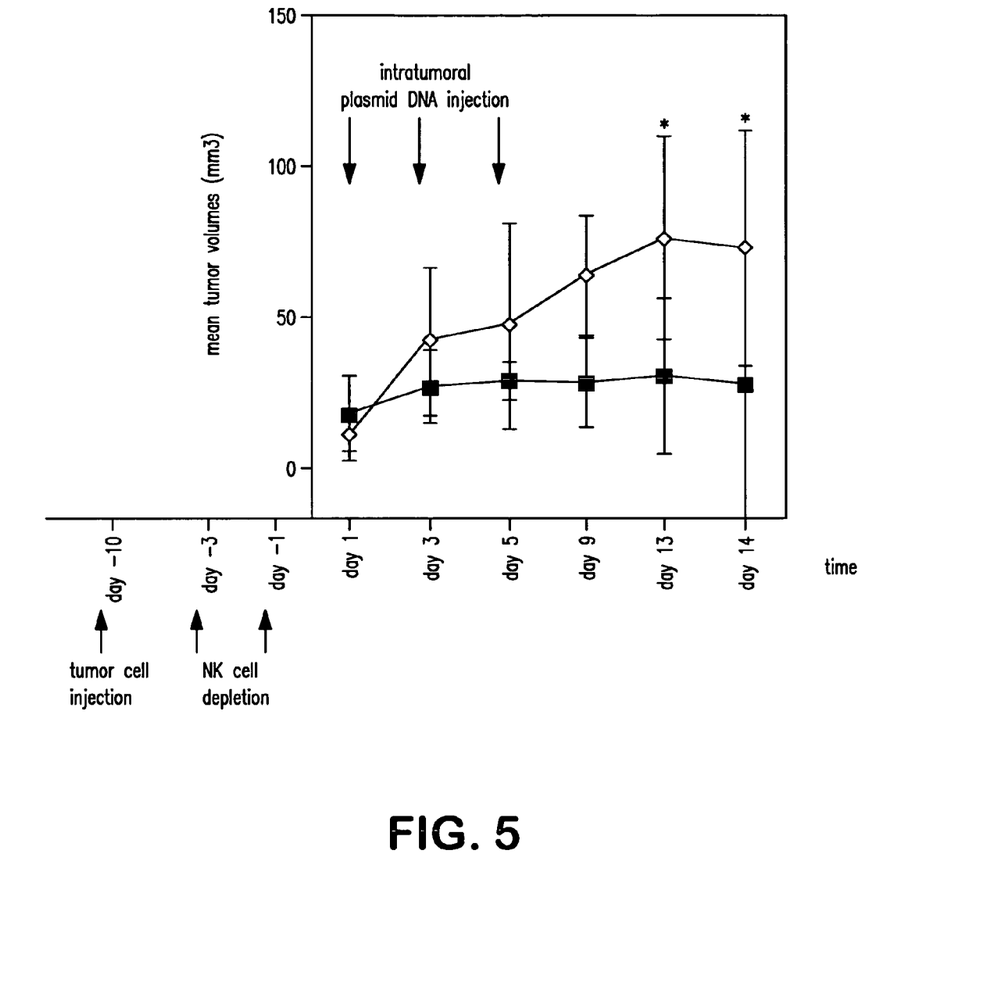
Figure 6A:
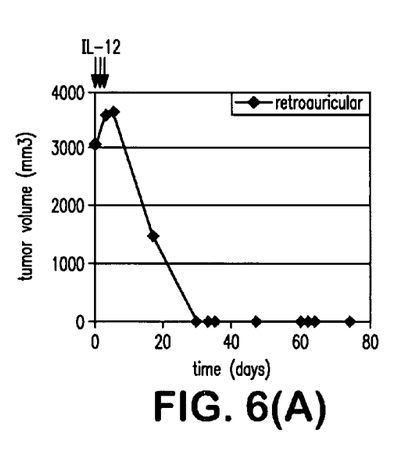
Figure 6B:
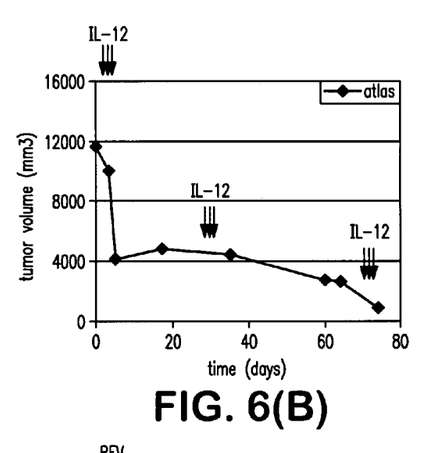
Figure 6C:
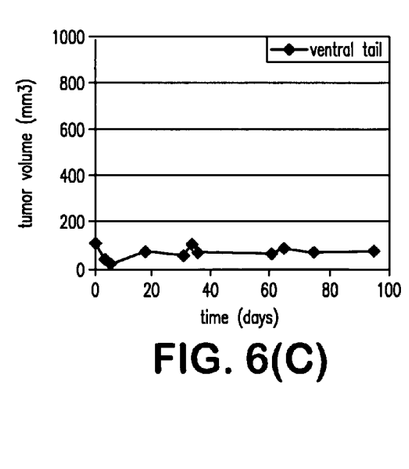
Figure 6D:
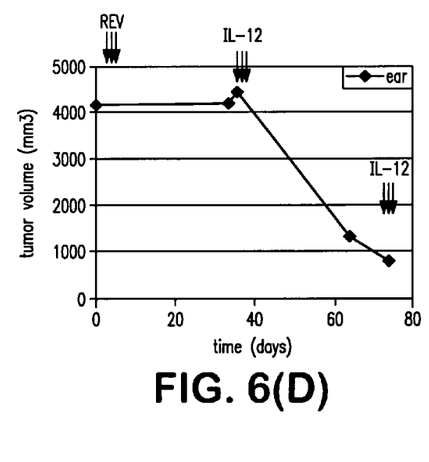

In order to determine the role of Natural Killer (NK)-cells as effector cells in the IL-12 DNA treatment depletion of NK-cells was performed by injecting intraperitoneally anti-asialo GM 1 rabbit antibodies directed to the surface ganglioside present on NK-cells. After 10 days palpable subcutaneous human MM 941209 tumors had established. Depletion of NK-cells was performed for three days and again one day prior to the therapy. Intratumoral injection of either empty vector or DNA encoding IL-12 was started at a mean tumor volume of 15 mm$^3$ and performed on day 1, 3 and 5. The smaller mean tumor volume was chosen to obtain better results in histologic evaluation. NK-depletion before the beginning of the DNA treatment lead to a significant retard in growth of subcutaneous tumors. The anti-tumor effect of the IL-12 encoding DNA was however reduced in NK-depleted mice. Until day 14 none of the animals was tumor free as opposed to two out of five in the group with normal NK-cells (FIG. 5). Thus NK-cells contribute to the anti-tumor effect of IL-12 encoding DNA treatment.

The results show that intratumoral injection of the IL-12 encoding DNA induced tumor regression of human malignant melanoma in nude mice and, in 2 out of 5 cases, complete eradication of the tumor. Growth retardation of subcutaneous mouse B16-melanomas was also induced by intralesional injection of plasmid DNA coding for IL-12 in C57BL/6 mice. The mechanism of this striking effect can be attributed to changes induced by the expression of IL-12 from the injected DNA in vivo.

The biological effects of IL-12 encompass stimulation of unspecific immunity, stimulation of specific immunity and inhibition or alteration of angiogenesis. With the above-described experiments it could be shown that the therapeutic effect of IL-12 encoding DNA probably depends predominantely on the anti-angiogenetic effect. Histologic analysis verified profound differences in the vasculature between treated and control animals. Peritumoral infiltrates of CD4+ cells and CD8+ cells as well as tumor infiltrating CD 4 and CD 8 lymphocytes induced by the IL-12 DNA treatment possibly play a role in the immune reaction. Furthermore, activation of NK-cells contributes to tumor rejection induced by IL-12 DNA treatment. The anti-tumor effect was reduced but not abrogated in mice lacking T- and NK-cells.

Changes induced in the tumor vasculature were characterized by elastin disruption with endothelial thickening and abrupt changes in vessel diameter as well as intravascular thrombosis. Large necrotic areas within the tumor tissue could be detected. Possible causes include apoptosis, necrosis due to hypoxia, lack of survival factors and/or release of death factors. At the beginning of the therapy vessels had already been established in the tumor. Thus we can conclude that the treatment regime not only affected the newly forming vessels but also preexisting tumor vasculature. These anti-angiogenetic effects do not depend on participation of T-cells as they were observed in Balb/c nude mice which lack thymus derived cells. Although injection of IFN-inducible protein-10 (IP-10) induced morphologically similar changes characterized by tumor necrosis in vivo with central necrosis, diffuse vascular damage with endothelial thickening and capillary thrombosis often distal of the necrotic tumor our results indicate that the effect of IL-12 coding DNA is not solely mediated by IP-10 as this CXC-chemokine inhibited tumor growth in euthymic but not in most nu/nu mice (Sgadari et al., Proc. Natl. Acad. Sci. USA 93 (1996), 13791–13796). Recombinant IP-10 did not induce complete tumor regression when injected intratumorally in subcutaneous Burkitt lymphomas (Sgadari et al., Proc. Natl. Acad. Sci. USA 93 (1996), 13791–13796). As compared to endostatin for example tumors did not regrow within the 5 to 14 days time span (O'Reilly et al., Cell 88 (1997), 277–285). A direct anti-proliferative effect of the in vivo expressed IL-12 can be excluded as recombinant IL-12 exhibits no direct anti-proliferative effect on melanoma cells as judged by the inability of the protein to alter tumor cell proliferation even at high concentrations (Sun Y et al., Gene Therapy 5 (1998), 481–490).

EXAMPLE 5

Tumor Regression Induced by Intra-tumoral Injection of DNA Coding for Human IL-12 into Equine Melanoma Metastases in White Horses White horses spontaneously develop tumors similar to human melanoma with primary tumors on lip or tail that subsequently metastasize to other parts of the skin and to various organs including small intestines, colon, bladder. So far, no treatment is applicated for tumors or metastases.

White horses that presented with several tumor nodules of metastatic melanoma were injected by needle intra-tumorally on day 1, 3 and 5 of each treatment cycle with 250 μg of plasmid DNA coding for human interleukin 12 (IL-12) or 250 μg control plasmid DNA containing the reverse human IL-12 insert. Some marker lesions were left untreated to determine spontaneous tumor evolvement without local treatment. Punch or trucat biopsies were performed on all marker and treated metastasis before therapy and on day 14 and 30 and biopsy specimens were examined histologically. Blood samples to assess hematological changes or alterations in serum chemistry were taken on days 1, 5, 14 and 30 of the treatment cycles. Tumors were measured using calipers and by ultrasound and tumor volumes were calculated according to the formula: small diameter$^2$×large diameter×0.5 (The results are shown in FIG. 6).

Tumor nodules injected with plasmid DNA coding for human interleukin 12 sharply decreased in volume. Histologically a swelling of cells could be observed and extracellular pigment as well as macrophages. Tumor tissue was replaced by scarry connective tissue. Tumors with no local treatment or tumors injected with control plasmid DNA containing reverse IL-12 showed no changes in volume.

EXAMPLE 6

Figure 7:
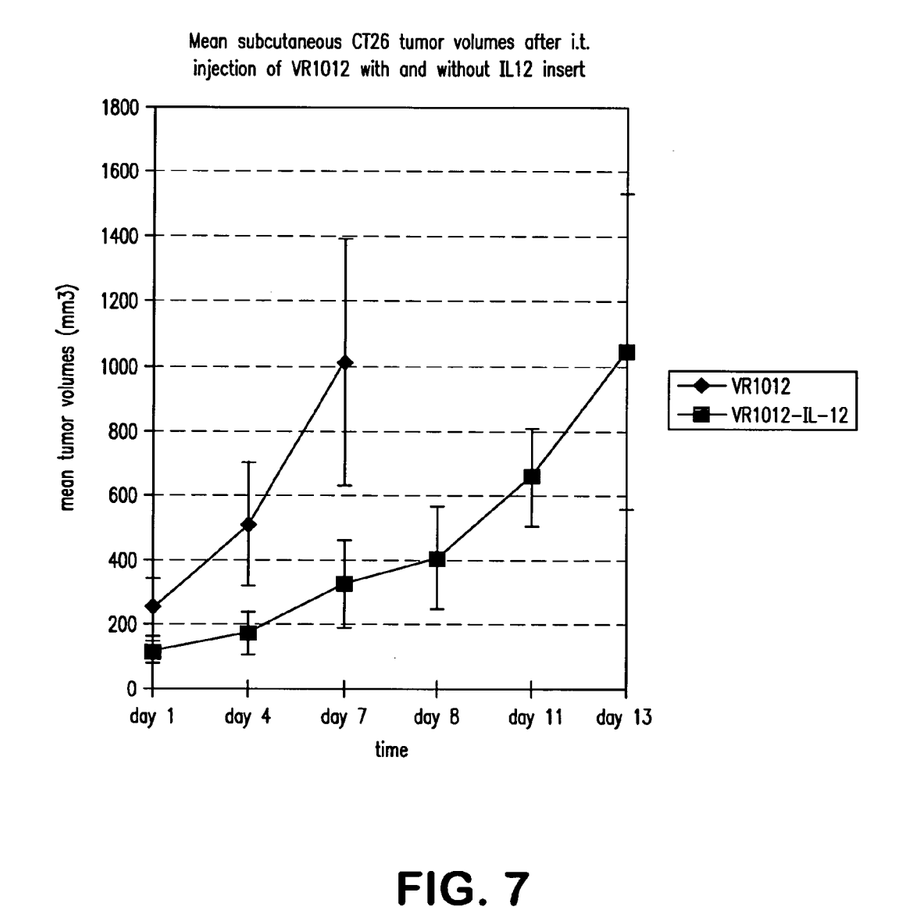
FIG. 7 shows mean tumor volumes and standard deviation of subcutaneous CT26 colon tumor after injection of IL-12 encoding DNA (squares) or control vector (rhombs). Mice were injected subcutaneously with 5×10$^4$ cells of the colon carcinoma cell line CT26. When palpable tumors were detected intratumoral therapy was realized on day 1, 3 and 5 administering each time 50 μg of IL-12 encoding VR1012-muIL-12 plasmid DNA (n=3) or control vector (n=3) by intratumoral injection.

Intratumoral Injection of IL-12 Encoding Plasmid DNA into Colon Carcinoma in Mice Tumor regression induced by intratumoral injection of DNA coding for murine IL-12 into colon carcinoma CT26 in mice tumors other than malignant melanoma were responsive to treatment with IL-12 DNA. Tumors derived from colon carcinoma CT26 cells in mice were grown by subcutaneous injection of 5×10$^4$ cells until palpable. Then they were treated by 50 μg of VR1012-muIL-12 DNA (n=3) or DNA plasmid VR1012 without insert (n=3) by intratumoral injection on day 1, 3 and 5. Tumor sizes were measured by caliper and plotted (FIG. 7).

The invention claimed is:

1. A method of treating a mammal having a tumor, comprising administering a pharmaceutically effective amount of a composition intra-tumorally to said mammal, wherein the composition comprises a naked nucleic acid molecule encoding an IL-12 polypeptide, the naked nucleic acid molecule not being complexed to viral structures, proteins, liposomes or other nucleic acid molecule delivery systems.

2. The method of claim 1, wherein the tumor is a highly vascularized tumor.

3. The method of claim 1 or 2, wherein the tumor is a sarcoma, carcinoma, melanoma or haemangioma.

4. The method of claim 1, wherein the composition further comprises an additional cytokine or a nucleic acid molecule encoding the additional cytokine.

5. The method of claim 4, wherein the additional cytokine is IL-15, IL-2, IFN-a, GM-CSF, IP-10, TNF or PAI-1.

6. The method of claim 1 or 4, wherein the composition further comprises a tumor-associated antigen protein or a nucleic acid molecule encoding a tumor-associated antigen.

7. The method of claim 1, wherein the composition further comprises a C- and G-rich oligonucleotide or a DNA oligonucleotide with antiproliferative effect.

8. The method of any one of claims 1, 2, 4 or 5, further comprising treating the mammal with chemotherapy.

9. The method of claim 8, wherein the chemotherapy is an anti-cancer chemotherapy.

10. The method of claim 8, wherein the chemotherapy is HAART (highly active anti-retroviral HIV therapy).

11. The method of claim 6, wherein the composition further comprises a C- and G-rich oligonucleotide or a DNA oligonucleotide with antiproliferative effect.

* * * * *

UNITED STATES PATENT AND TRADEMARK OFFICE
CERTIFICATE OF CORRECTION

| | |
|---|---|
| PATENT NO. | : 7,141,550 B2 |
| APPLICATION NO. | : 10/181794 |
| DATED | : November 28, 2006 |
| INVENTOR(S) | : Karin Mölling, Jan Schultz and Lucie Heinzerling |

It is certified that error appears in the above-identified patent and that said Letters Patent is hereby corrected as shown below:

On the Title page item (22) PCT Filing Date, change "Dec. 1, 2001" to --Jan. 12, 2001--.

Signed and Sealed this

Twenty-ninth Day of July, 2008

JON W. DUDAS
*Director of the United States Patent and Trademark Office*